United States Patent

Sebag et al.

[11] Patent Number: 4,657,556
[45] Date of Patent: Apr. 14, 1987

[54] HAIR COMPOSITION AND METHOD CONTAINING GLYCOSYLATED POLYETHERS

[75] Inventors: Henri Sebag, Paris; Guy Vanlerberghe, Claye Souilly, both of France

[73] Assignee: L'Oreal, Paris, France

[21] Appl. No.: 708,886

[22] Filed: Mar. 6, 1985

[30] Foreign Application Priority Data

Mar. 7, 1984 [FR] France ............... 84 03536

[51] Int. Cl.$^4$ ............ A61K 7/00; A61K 7/06; A61K 7/08; A61K 7/13
[52] U.S. Cl. .................................. 8/405; 8/406; 424/47; 424/70; 514/723; 514/777; 514/941
[58] Field of Search ............ 536/18.3; 424/47, 70; 514/723, 777, 941; 8/405, 406

[56] References Cited

U.S. PATENT DOCUMENTS

| | | | |
|---|---|---|---|
| 2,407,001 | 9/1946 | Griffin | 536/18.3 |
| 2,990,376 | 6/1961 | Bressler et al. | 536/18.3 |
| 3,357,970 | 12/1967 | Ulyatt | 536/18.3 |
| 3,445,525 | 5/1969 | Bormann et al. | 536/18.3 |
| 3,737,426 | 6/1973 | Throckmorton et al. | 536/18.3 |
| 4,183,917 | 1/1980 | Iwao et al. | 424/70 |
| 4,187,121 | 2/1980 | Herold | 536/18.3 |
| 4,380,502 | 4/1983 | Müller et al. | 536/18.3 |
| 4,446,313 | 5/1984 | Dix et al. | 536/18.3 |

FOREIGN PATENT DOCUMENTS

| | | | |
|---|---|---|---|
| 731638 | 4/1966 | Canada | 536/18.3 |
| 919665 | 1/1973 | Canada | 536/18.3 |
| 2110994 | 9/1972 | Fed. Rep. of Germany | 536/18.3 |
| 1468435 | 2/1973 | Fed. Rep. of Germany | 536/18.3 |
| 0024477 | 3/1981 | Japan | 514/777 |
| 0032809 | 2/1983 | Japan | 514/777 |
| 1277516 | 6/1972 | United Kingdom | 536/18.3 |

OTHER PUBLICATIONS

Cosmetics and Perfumery, 3/1974, vol. 89, pp. 33 and 34, Conrad.

*Primary Examiner*—Dale R. Ore
*Attorney, Agent, or Firm*—Cushman, Darby & Cushman

[57] ABSTRACT

Compounds of formula (I)

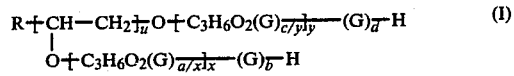

where
R = $C_{10-20}$ alkyl, alkenyl or alkylaryl;
G = $C_6H_{10}O_5$ radical derived from a hexose;
u = 0 or 1;
$0 \leq x \leq 10$; $0 \leq y \leq 10$; $1 \leq x+y \leq 10$;
a, b, c, d denote zero or a number less than or equal to 5, with the condition that
$1 \leq a+b+c+d \leq 5$ and $$0.7 \leq \frac{x+y}{a+b+c+d} \leq 4$$

These compounds are prepared by addition of (a+b+c+d) moles of an oside or alkylglucoside, or $$\frac{(a+b+c+d)}{2}$$

moles of diholoside, to a compound of formula (II)

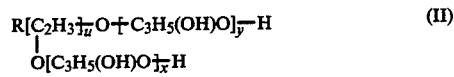

These compounds are surfactants which can be used in cosmetic and pharmaceutical compositions.

15 Claims, No Drawings

HAIR COMPOSITION AND METHOD CONTAINING GLYCOSYLATED POLYETHERS

The invention has as its subject new glycosylated polyethers, the process for the preparation thereof and the use thereof.

The invention also has as its subject new polyhydroxylated non-ionic surfactants in which the hydrophilic sequence contains groups derived from glycerol and oses, the process for the preparation of these products and their use in the preparation of cosmetic and pharmaceutical compositions.

Surfactants, or surface-active compounds, containing hydrophilic sequences derived from glycerol have already been described, especially in French Pat. Nos. 1,477,048, 1,531,010, 2,027,585 and 2,091,516.

These French patents correspond to the following U.S. Pat. Nos: Nos. 3,578,719, 3,708,364, 3,840,606 and 3,821,372.

These compounds are prepared by (poly)addition to a lipophilic compound containing at least one reactive hydrogen atom, and preferably to an alcohol, an alpha-diol or an alkylphenol, of:

- a glycerol epihalohydrin, followed by a hydrolysis reaction;
- tert-butyl glycidyl ether, followed by replacement of the tert-butyl group by a hydroxyl group, or
- glycidol.

There have also been described alkyl glucosides and alkyloligosaccharides obtained by reacting higher monoalcohols with a monosaccharide or polysaccharide. The latter are also called oses or sugars.

These alkylglucosides and alkyloligosaccharides are very difficult to prepare satisfactorily on account of the lack of miscibility between fatty alcohols and sugars, this miscibility being poorer the longer the hydrocarbon chain.

An attempt has been made to overcome these problems by involving a solvent in the reaction between the alcohol and the sugars, or by using an excess of alcohol.

French Pat. No. 2,005,596 (Atlas Chemical Industries) teaches the use of an aliphatic glycol having from 3 to 5 carbon atoms as a solvent. U.S. Pat. No. 3,839,318 (Rohm and Haas) teaches the use of an excess of alcohol, the proportion of alcohol increasing with the molecular weight of the latter.

This excess alcohol and/or solvent must then be removed. This removal is rendered very difficult by virtue of the fact that the products resulting from the reaction are very hard and solidify. For this reason, the separation and purification reactions are difficult to carry out.

The process according to the invention enables these disadvantages to be overcome by reacting sugars with compounds which contain a polyglycerylated hydrophilic portion, and this permits better contact and facilitates the reaction. Furthermore, the resulting products are generally less hard and remain fluid or pasty until the end of the reaction, and they can be directly used without the need for special purification.

The products which result from these reactions are non-ionic surfactants which possess several advantages relative to the compounds of the state of the most closely related art.

These products are, in fact, of lower cost than the non-ionic compounds derived exclusively from fatty alcohols and glycerol. Surprisingly, they are less demaging, and some of their physicochemical properties, such as the foaming power or dispersant power especially towards dyes, are preserved or even improved.

The products according to the invention can be represented by the general formula (I)

$$R \mhyphen (CH \mhyphen CH_2)_u \mhyphen O \mhyphen (C_3H_6O_2(G)_{c/y})_y \mhyphen (G)_d \mhyphen H$$
$$| \quad O \mhyphen (C_3H_6O_2(G)_{a/x})_x \mhyphen (G)_b \mhyphen H$$

where
- R denotes a $C_{10}$-$C_{20}$ alkyl, alkenyl or alkylaryl radical,
- G denotes a $C_6H_{10}O_5$ radical derived from an aldose of formula $C_6H_{12}O_6$, such as α- or β-glucose, α- or β-galactose, or mannose
- u denotes zero or the number 1,
- x denotes zero or an integer or decimal less than or equal to 10,
- y denotes an integer or decimal equal to or less than 10, with the condition that $1 \leq x+y \leq 10$,
- a, b, c and d, which may be identical or different, denote zero or an integer or decimal less than or equal to 5, with the condition that:
(i) $1 \leq a+b+c+d \leq 5$
(ii)
$$0.7 \leq \frac{x+b}{a+b+c+d} \leq 4$$

when u denotes zero, each of the symbols x, a, b denotes zero and y denotes an integer or decimal from 1.5 to 10; when R denotes alkylaryl, each of the symbols u, x, a and b denotes zero.

Among the preferred compounds there occur those for which
$1.5 \leq x+y \leq 3$

The unit $[C_3H_6O_2(G)_{a/x}]$ mainly denotes the three structures below:

$$\mhyphen (CH_2 \mhyphen CH \mhyphen O)\mhyphen ; \qquad \mhyphen (CH \mhyphen CH_2 \mhyphen O)\mhyphen ;$$
$$\quad | \qquad\qquad\qquad\qquad |$$
$$CH_2 \mhyphen O \mhyphen (G)_{a/x} \qquad CH_2 \mhyphen O \mhyphen (G)_{a/x}$$
$$\text{I(a)} \qquad\qquad\qquad \text{I(b)}$$

$$\mhyphen (CH_2 \mhyphen CH \mhyphen CH_2 \mhyphen O)\mhyphen$$
$$| $$
$$O \mhyphen (G)_{a/x}$$
$$\text{I(c)}$$

The unit $[C_3H_6O_2(G)_{c/y}]$ mainly denotes the three structures below:

$$\mhyphen (CH_2 \mhyphen CH \mhyphen O)\mhyphen ; \qquad \mhyphen (CH \mhyphen CH_2 \mhyphen O)\mhyphen ;$$
$$\quad | \qquad\qquad\qquad\qquad |$$
$$CH_2 \mhyphen O(G)_{c/y} \qquad CH_2 \mhyphen O \mhyphen (G)_{c/y}$$
$$\text{I(d)} \qquad\qquad\qquad \text{I(f)}$$

$$\mhyphen (CH_2 \mhyphen CH \mhyphen CH_2 \mhyphen O)\mhyphen$$
$$|$$
$$O \mhyphen (G)_{c/y}$$
$$\text{I(g)}$$

G denotes a glucosyl radical of formula:

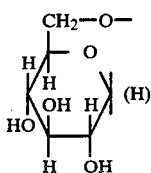

or a galactosyl radical of formula:

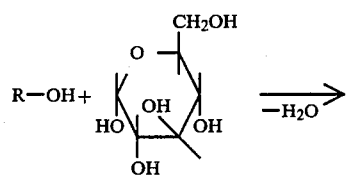

For example, the structural formula of the unit I(a) can be shown in the following manner:

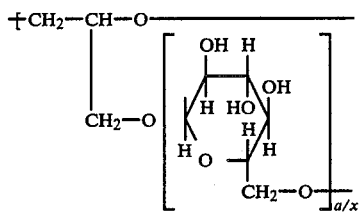

and a similar formula can be written with the galactosyl radical, and also for the units I(b), I(c), I(d), I(f) and I(g).

The products according to the invention are obtained by condensation, in the presence of a strong acid, of $(a+b+c+d)=S$ mole(s) of ose or oside or of S/2 mole(s) of diholoside per mole of intermediate product of formula

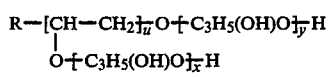       (II)

When the condensation of ose, oside or diholoside with the glycerolated intermediate compound of formula (II) is performed in acid medium, the hemiacetal group of the sugar react, that is to say the OH group numbered (1)

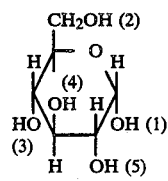

to form glycosides, so that the products of formula (I) possess almost no reducing properties as regards Fehling's solution.

In the intermediate compounds of formula (II), the unit [$C_3H_5(OH)O$] mainly denotes the three structures below

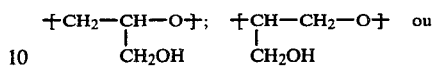

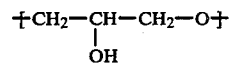

The formula (II) can also include limited quantities of other isomers resulting from the preparation processes described in French Pat. Nos. 1,477,048; 1,531,010; 2,027,585 and 2,091,516, and U.S. Pat. Nos. 3,578,719; 3,708,364; 3,840,606 and 3,821,372.

Compounds of formula (II) can be prepared by one of the processes below:

(i) polyaddition per mole of a hydroxylated compound

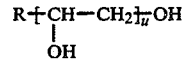

of $x+y$ moles of glycerol epihalohydrin in the presence of an acidic catalyst such as boron fluoride, stannic chloride or antimony pentachloride, at a temperature between 25° and 120° C. and preferably between 40° and 100° C., followed by hydroxylation of the halogenated derivatives obtained, by reaction with an alkali metal salt of a carboxylic acid, and preferably with sodium acetate or potassium acetate, advantageously using as solvent a glycol such as propylene glycol, dipropylene glycol, ethylene glycol, diethylene glycol, hexylene glycol or glycol ethers such as 2-butoxyethanol, at a temperature between 150° and 200° C. and preferably between 180° and 190° C., the acetic acid ester formed then being hydrolyzed. This preparation process is described in greater detail in French Pat. Nos. 1,477,048 and 1,531,010.

(ii) polyaddition per mole of compound of formula

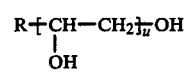

of $(x+y)$ moles of tert-butyl glycidyl ether, R, u, x and y having the same significance as above, in the presence of an acidic catalyst such as $BF_3$, $SnCl_4$ or $SbCl_5$ in the proportion of 0.1 to 3% relative to the total reacting mass, at a temperature of 40° to 120° C., or in the presence of a basic catalyst in the proportion of 0.1 to 10% relative to the total reacting mass and at a temperature of 120° C. to 180° C. in the absence of solvent or in the presence of an inert solvent. In the products obtained, the tert-butoxy group is replaced by hydroxyl groups in the presence of strong acid such as sulphoacetic acid, and optionally in the presence of water, at a temperature of 50° to 120° C. This process is described in greater detail in French Pat. No. 2,027,585 or in U.S. Pat. No. 3,846,106.

(iii) polyaddition per mole of α-diol of formula R—CHOH—$CH_2OH$, where R has the same significance as in formula (II), of $(x+y)$ moles of glycidol, in an inert atmosphere in the presence of a basic catalyst chosen preferably from alkali metal hydroxides and alkali metal alcoholates, preferably sodium or potassium alcoholates, in the proportions of 0.5 to 10 moles% relative to the diols used, at a temperature of 120°–180° C. and preferably from 140° to 160° C. R, x and y have the same significance as in formula (II). This preparation process is described in greater detail in French Pat. No. 2,091,516 or in U.S. Pat. No. 3,821,372.

By this process there are obtained compounds of formula (II) where $u=1$, x and y denote an integer or decimal less than 10 and $1 \leq x+y \leq 10$.

(iv) polyaddition per mole of hydroxylated compound of $(x+y)$ moles of glycidol in the presence of an acidic catalyst such as boron trifluoride, tin tetrachloride or antimony pentachloride, at a temperature between 50° and 120° C. This preparation process is described in greater detail in French Pat. No. 2,169,787. As hydroxylated compound, there can be used, for example, a compound of formula:

where R, u, x and y have the significance given above.

The condensation of ose or oside with a compound of formula (II) is carried out at a temperature of 90°–140°0 C. and preferably 100°–130° C. in the presence of an inorganic or strong organic acid. Among these acids, sulphuric acid, phosphoric acid or p-toluenesulphonic acid is advantageously used. The reaction can be carried out at ordinary pressure and/or under reduced pressure.

As ose or oside, glucose and galactose are preferably used, and as diholoside lactose, sucrose, maltose and cellobiose are preferably used. Alkylglucosides in which the alkyl group contains from 1 to 4 carbon atoms, such as for example methylglucoside, ethylglucoside, and the like, are also used.

These sugars can be used in the crystallized or anhydrous state or in the form of hydrate, and also in the form of aqueous solution.

The condensation reactions of aldoses or alkylglycosides take place with removal of water or $C_{1-4}$ alcohol.

To promote the removal of water or $C_{1-4}$ alcohol, the reaction is carried out, at least in its final phase, under reduced pressure.

During the condensation reaction, there is formed a mixture of compounds all corresponding to the general formula (I) but for which the number of molecules (G) bound per molecule of formula (II) can be greater than, equal to or less than the average statistical value S ($S=a+b+c+d$) corresponding to the number of ose or oside molecules (or to half the number of diholoside molecules) used for one molecule of compounds (II).

At the reaction temperatures, the products of formula (I) generally take the form of paste, which becomes ropy on being cooled and gives hard, amber-colored waxes at room temperature.

These products are soluble or dispersible in water, depending on the length of the hydrophilic portion relative to the lipophilic portion.

Depending on their constitution, they can have wetting, foaming, dispersant, solubilizing and/or emulsifying properties.

They can be used in cosmetic or pharmaceutical compositions at concentrations generally between 0.1 and 30% of active substances and preferably between 0.5 and 20% of active substances.

These cosmetic or pharmaceutical compositions can take the form of an aqueous or hydroalcoholic solution or dispersion, or the form of a paste, gel, emulsion (cream or milk), solid or aerosol.

By hydroalcoholic solutions, there are understood solutions containing $C_{1-6}$ alcohols or $C_{2-6}$ diols or glycol ethers such as ethers of ethylene glycol, propylene glycol, diethylene glycol or dipropylene glycol.

The cosmetic or pharmaceutical compositions according to the invention can contain one or more constituents chosen from anionic, cationic, non-ionic, amphoteric and zwitterionic surfactants, anionic, cationic, non-ionic and amphoteric polymers, foam synergists, foam stabilizers, proteins, thickeners, opacifying agents, superfatting agents, preservatives, reducing agents, oxidizing agents, solvents, electrolytes and propellants.

The cosmetic compositions according to the invention can also contain a dye and/or pigment.

The cosmetic compositions can take the form of shampoos, coloring shampoo, after-shampoo composition, dyeing composition, hair conditioning composition, and the like. The invention will be better understood by means of the non-limitative examples below:

EXAMPLE 1

Preparation of a mixture of compounds of general formula (I) in which:
R denotes $C_{10}H_{21}$;
u=zero;
y=1.5;
c+d=1.5.

1—Preparation of the mixture of polyglycerol alkyl ethers of formula (II)

Polyaddition of 138.75 g of epichlorohydrin (1.5 mole) to 158 g (1 mole) of 1-decanol in the presence of 0.59 ml of tin tetrachloride and hydrolysis of the products obtained, according to the process described in French Pat. No. 1,477,048 and in U.S. Pat. No. 3,578,719. A golden yellow viscous product is obtained.

2—Preparation of the mixture of compounds of formula (I) according to the invention To 53.8 g (0.2 mole) of product of formula (II) thus obtained, 2.5 ml of 4N hydrochloric acid are added and the mixture is then dehydrated by heating it under reduced pressure after 15 minutes' stirring.

0.65 g of p-toluenesulphonic acid is added, followed by 54 g of anhydrous glucose (0.3 mole) in small portions under a stream of nitrogen at 100°–110° C.

After the addition of approximately each quarter of the amount of glucose, the reactor is taken to reduced pressure for 3 to 5 minutes.

Total time of addition: 2 hours 30 minutes.

After the addition is complete, the reacting mass is heated for a further 1 hour 30 minutes at 110° C. under reduced pressure.

There is thus obtained an amber-colored mass fluid when hot and ropy on cooling, which is soluble in water.

EXAMPLE 2

Preparation of a mixture of compounds of general formula (I) in which:
R denotes $C_{12}H_{25}$;
u=0;

$y = 2$;
$c + d = 2$.

1—Preparation of the mixture of polyglycerol alkyl ethers of formula (II)

Polyaddition of 185 g of epichlorohydrin (2 moles) to 186 g of 1-decanol in the presence of 0.85 ml of $BF_3$ etherate and hydrolysis of the polychlorinated compounds according to the process described in French Pat. No. 1,477,048 and U.S. Pat. No. 3,578,719; there is thus obtained a pasty liquid product which is dispersible in water.

2—Preparation of the mixture of compounds of formula (I) according to the invention To 100.2 g of product of formula (II) obtained, 5 ml of 4N hydrochloric acid are added. The mixture is then dehydrated under reduced pressure. 1.1 g of p-toluenesulphonic acid is then added, followed by 216 g of 50% strength glucose solution added dropwise at 115° C. under a stream of nitrogen.

After approximately 150 g of solution are added, the reactor is taken to reduced pressure for approximately 5 minutes.

Time of addition: 2 hours.

After the addition is complete, the reacting mass is heated for a further 45 minutes to 120° C. under a pressure of 30 mm of Hg (4 kPa).

There is thus obtained a brown product, a fluid when hot and ropy on being cooled, which is soluble in water.

The cloud point of 0.5% strength solution in water is 75° C.

EXAMPLE 3

Preparation of a mixture of compounds of general formula (I) in which:
R denotes $C_{10}H_{21}$;
$u = 0$;
$y = 3.5$;
$c + d = 2$.

1—Preparation of the mixture of polyglycerol alkyl ethers of formula (II)

Polyaddition of 277.5 g of epichlorohydrin (3 moles) to 158 g of 1-decanol in the presence of 0.87 ml of tin tetrachloride, and hydrolysis of the polychlorinated compounds according to the process described in French Pat. No. 1,477,048 and U.S. Pat. No. 3,578,719.

There is thus obtained a very viscous amber-colored product which is soluble in water.

2—Preparation of the mixture of compounds of formula (I) according to the invention To 56 g (0.13 mole) of product of formula (II) thus obtained, 2.5 ml of 4N hydrochloric acid are added. The mixture is then dehydrated under reduced pressure. 0.52 g of para-toluenesulphonic acid is then added, followed by 96.5 g of 50% strength glucose solution (0.268 mole) added dropwise at 90°/110° C. under a pressure of 40 mm of Hg (5.33 kPa).

Time of addition: 2 hours.

After the addition is complete, the reacting mass is heated for a further 1 hour at 115°/120° C. under 40 mm of Hg (5.33 kPa). There is thus obtained a clear amber-colored product, fluid when hot and ropy on being cooled, which is soluble in water.

The cloud point of a 0.5% strength solution in water containing 25% NaCl is higher than 100° C.

EXAMPLE 4

Preparation of a mixture of compounds of general formula (I) in which:
R = hydrocarbon radical derived from oleic alcohol;
$u = 0$;
$y = 2$;
$c + d = 1.5$.

1—Preparation of the mixture of polyglycerol alkyl ethers of formula (II)

Polyaddition of 185 g of epichlorohydrin (2 moles) to 268 g (1 mole) of oleic alcohol in the presence of 1.13 ml of $BF_3$ etherate, and hydrolysis of the polychlorinated compounds according to the process described in French Pat. No. 1,477,048 and U.S. Pat. No. 3,578,719.

There is thus obtained a pale amber viscous product which is insoluble in water.

2—Preparation of the mixture of compounds of formula (I) according to the invention To 50 g (0.13 mole) of products of formula (II) thus obtained, 2.5 ml of 4N hydrochloric acid are added. The mixture is then dehydrated under reduced pressure. There are then added 2 g of a 50% strength aqueous solution of para-toluenesulphonic acid, followed by 52.2 g of a 50% strength glucose solution added dropwise in four portions at 115° C. under a stream of nitrogen. After the addition of each of the portions, the reactor is taken to reduced pressure for approximately 3 minutes.

Time of addition: 2 hours.

After the addition is complete, the reacting mass is heated for a further 1 hour at 120° C. under 25 mm of Hg (3.33 kPa).

There is thus obtained a clear, pale amber-colored product, fluid when hot and ropy on being cooled, giving a slightly brittle product dispersible in water.

EXAMPLE 5

Preparation of a mixture of compounds of general formula (I) in which:
R denotes $C_{10}H_{21}$;
$u = 1$;
$(x + y) = 3.5$;
$a + b + c + d = 2$.

1—Preparation of the mixture of compounds of formula (IIb)

To 202 g of 1,2-dodecanediol, there are added 5 g of 40% strength aqueous NaOH solution and then, at 150° C., 260 g of glycidol, according to the process described in French Pat. No. 2,091,516 and in U.S. Pat. No. 3,821,372. The products obtained take the form of a hard paste which is soluble in water.

2—Preparation of the mixture of compounds of formula (I) according to the invention After the neutralization of the catalyst with hydrochloric acid, there are added 3.2 g of p-toluenesulphonic acid (diluted to 6 g with water) to 92.2 g of products of formula (II) (0.2 mole) obtained above, followed by 72 g (0.2 mole) of lactose added in small portions at 110° C.

Time of addition: 1 hour 30 minutes.

The heating is continued under reduced pressure for 30 minutes after the addition is complete, until the water formed has been completely removed. The end products take the form of a brown mass, hard when cold, which is soluble in water.

EXAMPLE 6

Preparation of a mixture of compounds of general formula (I) in which:
R denotes

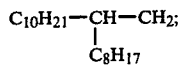

$u=0$;
$y=6$;
$c+d=5$.

1—Preparation of the mixture of polyglycerol alkyl ethers of formula (II)

Polyaddition of 555 g of epichlorohydrin (6 moles) to 298 g (1 mole) of 2-octyl-1-dodecanol in the presence of 2.6 ml of $BF_3$ etherate, and hydrolysis of the polychlorinated compounds, according to the process described in French Pat. No. 1,477,048 and U.S. Pat. No. 3,578,719.

There is thus obtained a brown pasty product which is insoluble in water.

2—Preparation of the mixture of compounds of formula (I) according to the invention To 44.5 g (0.06 mole) of product of formula (II) thus obtained, 2.4 ml of 6N hydrochloric acid are added. The product is dehydrated.

1.8 g of 50% strength p-toluenesulphonic acid solution are then added, followed by 54 g (0.3 mole) of anhydrous glucose added in small portions at 110°/115° C.

The reactor is taken to reduced pressure for 3 to 5 minutes on 3 or 4 occasions during the addition, which lasts a total of 4 hours.

After the addition is complete, the reacting mass is heated for a further 1 hour at 115° C. under a pressure of 20 mm of Hg (2.66 kPa).

There is thus obtained a clear amber-colored mass which becomes ropy on being cooled, the aqueous solutions of which are opalescent.

EXAMPLE 7

Preparation of a mixture of compounds of general formula I in which:
R denotes a nonylphenyl radical;
$u=0$;
$y=2$;
$c+d=2$.

1-Preparation of the mixture of polyglycerol alkyl ethers of formula (II)

Polyaddition of 185 g of epichlorohydrin (2 moles) to 213 g (1 mole) of nonylphenol in the presence of 1 ml of $BF_3$ etherate, and hydrolysis of the polychlorinated compounds according to the process described in French Pat. No. 1,477,048 and U.S. Pat. No. 3,578,719.

There is thus obtained a clear, amber-colored very viscous product.

2—Preparation of the mixture of compounds of formula (I) according to the invention To 18.5 g of products of formula (II) thus obtained, 2 ml of 4N hydrochloric acid are added. After dehydration under reduced pressure, 0.75 g of 50% strength p-toluenesulphonic acid solution is added, followed by 54 g of 50% strength glucose solution added dropwise at 115° C. under a stream of nitrogen.

The reactor is taken to a pressure of 30 mm of Hg (4 kPa) for 3 minutes after each portion of approximately 25% of the amount of glucose.

Total time of addition: 2 hours 30 minutes.

After the addition is complete, the reacting mass is heated for approximately 15 minutes at 120° C. under a pressure of 30 mm of Hg (4 kPa).

There is thus obtained an amber-colored mass which is brittle when cold.

EXAMPLE 8

Preparation of a mixture of compounds of general formula I in which:
R=hydrocarbon radical derived from oleic alcohol;
$u=0$;
$y=4$;
$c+d=2$.

1—Preparation of the mixture of polyglycerol alkyl ethers of formula (II)

Polyaddition of 370 g of epichlorohydrin (4 moles) to 268 g (1 mole) of oleic alcohol in the presence of 1.6 ml of $BF_3$ etherate, and hydrolysis of the polychlorinated compounds according to the process described in French Pat. No. 1,477,048 and U.S. Pat. No. 3,578,719. There are thus obtained pasty, amber-colored products which are dispersible in water.

2—Preparation of the mixture of compounds of formula (I) according to the invention To 113 g (0.2 mole) of products thus obtained, 4.5 ml of 6N hydrochloric acid are added. The mixture is then dehydrated under reduced pressure. There are then added 5.5 g of a 50% strength aqueous p-toluenesulphonic acid solution, followed by 77.6 g of methylglucose added in small portions at 115° C. under a stream of nitrogen. After one half of the addition, the reactor is taken to a pressure of 25 mm of Hg (3.33 kPa) for approximately 20 minutes.

Time of addition: 3 hours 30 minutes.

After the addition is complete, the reacting mass is heated to 120° C. for 15 minutes at ordinary pressure, and then for a further 1 hour under a pressure of 25 mm of Hg (3.33 kPa).

There is thus obtained a clear brown product, fluid when not and ropy on being cooled, giving a brittle product which is soluble in water.

EXAMPLES OF APPLICATIONS

EXAMPLE A1: SHAMPOO

| | |
|---|---|
| Mixture of compounds of Example 2 | 7.6 g AS[1] |
| Lauric alcohol monosulphosuccinate polyethoxylated with 3 moles of ethylene oxide, sold in 40% strength AS aqueous solution under the name Setacin 103 Special by the company ZSCHIMMER & SCHWARTZ | 3.9 g AS |
| Carboxymethylcellulose sold under the name carboxymethylcellulose 7M8/SF by the company HERCULES | 2 g |
| NaOH | q.s. pH 7.5 |
| Water | q.s. 100 g |

[1]AS = active substance

Applied to dirty hair, this shampoo develops an abundant foam. After being rinsed, the hair is soft and non-electric.

EXAMPLE A2: SHAMPOO

Similar results are obtained by replacing the mixture of compounds of Example 2 by the mixture of compounds of Example 5.

EXAMPLE A3: SHAMPOO

| | |
|---|---|
| Mixture of compounds of Example 1 | 12 g AS |
| Lauric/myristic diethanolamide sold under the name Comperlan MLD by the company HENKEL | 2 g AS |
| NaOH | q.s. pH 6.6 |
| Water | q.s. 100 g |

This shampoo develops a soft and abundant foam and does not irritate the eyes.

EXAMPLE A4: SHAMPOO

| | |
|---|---|
| Mixture of compounds of Example 3 | 10 g AS |
| Potassium salt of the condensation product of collagen hydrolysate and fatty acid sold in approximately 30% strength AS aqueous solution under the name LAMEPON S by the company GRUNAU | 2 g AS |
| Coco diethanolamide sold under the name Comperlan KD by the company HENKEL | 2 g AS |
| NaOH | q.s. pH 7.5 |
| Water | q.s. 100 g |

This shampoo makes the hair soft and supple.

EXAMPLE A5: AFTER-SHAMPOO, TO BE RINSED, PRESENTED IN AEROSOL FORM

| | |
|---|---|
| Mixture of compounds of Example 3 | 0.8 g AS |
| Distearyldimethylammonium chloride | 0.8 g AS |
| Lauric/myristic diethanolamide sold under the name Comperlan LMD by the company HENKEL | 0.4 g AS |
| NaOH | q.s. pH 8.5 |
| Water | q.s. 100 g |

This composition is packaged in an aerosol can according to the following scheme:

| | |
|---|---|
| Composition | 90% |
| Freons 12/114 (43:57) propellant | 10% |
| | 100% |

The foam is applied to a clean, damp head of hair. After 2 to 3 minutes' exposure, the hair is rinsed; it is then easy to disentangle and soft.

EXAMPLE A6

Similar results are obtained by replacing the compounds of Example 3 in the above composition by the compounds of Example 5.

EXAMPLE A7: AFTER-SHAMPOO, TO BE RINSED

| | |
|---|---|
| Mixture of compounds of Example 3 | 1 g AS |
| Cetyl and stearyl alcohols (30:70) ethoxylated with 33 moles of ethylene oxide; sold under the name Simulsol C.S. by the company SEPPIC | 5 g AS |
| Cetyl and stearyl alcohols (30:70) sold under the name Sipol 16/18 S3 by the company HENKEL | 2.5 g AS |
| Copolymer of vinylpyrrolidone and methylvinylimidazolinium chloride sold in 40% strength aqueous solution under the name Luviquat FC 905 by the company BASF | 1 g AS |
| Carboxymethylcellulose sold under the name carboxymethylcellulose 7M8/SF by the company HERCULES | 1.6 g AS |
| HCl | q.s. pH 7.55 |
| Water | q.s. 100 g |

This cream is applied to clean, damp hair for several minutes. After being rinsed, the hair is easily disentangled and is soft.

EXAMPLE A8: COLOURING COMPOSITION

| | |
|---|---|
| 2-(N—Methylamino)-5-[N,N—bis(β-hydroxyethyl)amino]nitrobenzene | 0.8 g |
| 3-Methoxy-4-[N—(β-hydroxyethyl)amino]-nitrobenzene | 0.15 g |
| 2-Amino-4-methyl-5-[N—(β-hydroxyethyl)amino]nitrobenzene | 0.02 g |
| Blue extra celliton sold by the company BASF (corresponds to CI 64,500 - Disperse blue 1) | 0.1 g |
| Black diazoacetoquinone BSNZ 1350 sold by the company PCUK (corresponds to Disperse black 5) | 0.1 g |
| Lauric diethanolamide | 1.5 g |
| Lauric acid | 2.0 g |
| Mixture of compounds of Example 4 | 2 g |
| Propyl paraoxybenzoate | 0.05 g |
| Methyl paraoxybenzoate | 0.1 g |
| Ethylene glycol monoethyl ether | 5.0 g |
| Hydroxyethylcellulose sold under the name NATROSOL 250 HRR by the company HERCULES | 1.0 g |
| Meonothanolamine | q.s. pH 9.5 |
| Demineralized water | q.s. 100 g |

This colouring composition is applied for 30 minutes to a head of light brown hair having glints of red. After being rinsed, the hair is dyed a natural shade of light brown. In particular, the red glints have disappeared.

EXAMPLE A9: COLORING COMPOSITION

The same composition is prepared as above, except that the mixture of compounds of Example 6 is used in place of the mixture of compounds of Example 4. A similar result is obtained.

EXAMPLE A10: COLORING COMPOSITION

| | |
|---|---|
| Safranine RAL sold by the company PCUK (corresponds to CI 50,240 - Basic red 2) | 0.1 g |
| Rhodamine B extra concentrate sold by the company ACNA (corresponds to CI 45,170 - Basic violet 10) | 0.05 g |
| Acridine orange (corresponds to CI 46,005 - Basic orange 14) | 0.1 g |
| Arianor madder sold by the company MORTON (corresponds to CI 12,245 - Basic red 76) | 0.05 g |
| 2-[N—(β-aminoethyl)amino]-5-(β-hydroxyethyloxy)nitrobenzene | 0.2 g |
| Coco monoethanolamide | 4 g |
| Lauric alcohol treated with 23 moles of ethylene oxide | 4 g |
| Mixture of compounds of Example 4 | 1 g |
| Propyl paraoxybenzoate | 0.05 g |
| Methyl paraoxybenzoate | 0.1 g |

-continued

| | |
|---|---|
| Hydroxyethylcellulose sold under the name NATROSOL 250 HRR by the company HERCULES | 1.0 g |
| Triethanolamine | q.s. pH 9 |
| Demineralized water | q.s. 100 g |

This composition is applied for 25 minutes to brown hair. After rinsing, the hair possesses an intense red coppery glint.

EXAMPLE A11: COLOURING COMPOSITION

| | |
|---|---|
| Mixture of compounds of Example 4 | 5 g |
| 3-Methoxy-4-[N—(β-hydroxyethyl)amino]-nitrobenzene | 0.1 g |
| 2-[N—(β-hydroxyethyl)amino]-5-(hydroxy)nitrobenzene | 0.4 g |
| 2-Amino-5-(hydroxy)nitrobenzene | 0.1 g |
| Lauric acid | 2.0 g |
| Propyl paraoxybenzoate | 0.05 g |
| Methyl paraoxybenzoate | 0.1 g |
| Ethylene glycol monoethyl ether | 5 g |
| Hydroxyethylcellulose sold under the name NATROSOL 250 HRR by the company HERCULES | 1.0 g |
| Monoethanolamine | q.s. pH 9.5 |
| Demineralized water | q.s. 100 g |

This composition applied for 30 minutes to light brown hair gives the hair a red coppery glint after rinsing.

EXAMPLE A12: COLORING SHAMPOO

| | |
|---|---|
| 2-Amino-5-[N—(β-hydroxyethyl)amino]-nitrobenzene | 0.30 g |
| 2-Amino-5-(N—methylamino)nitrobenzene | 1.10 g |
| 2-Amino-3-(methyl)nitrobenzene | 0.6 g |
| 3-Hydroxy-4-[N—(β-hydroxyethyl)amino]-nitrobenzene | 0.1 g |
| Blue victoria BSA extra sold by the company PCUK (corresponds to CI 44,045 Basic blue 26) | 0.05 g |
| Mixture of compounds of Example 4 | 4 g |
| Ammonium lauryl sulphate sold under the name SACTIPON 286 by the company LEVER | 20 g |
| Preservative consisting of a mixture of 5-chloro-2-methyl-4-isothiazolin-3-one, 2-methyl-4-isothiazolin-3-one and magnesium chloride and calcium chloride in 1.5% strength aqueous solution, sold under the name KATHON GC by the company ROHM & HAAS | 0.05 g |
| Hydroxyethylcellulose sold under the name NATROSOL 250 HRR by the company HERCULES | 1 g |
| NaOH | q.s. pH 8 |
| Demineralized water | q.s. 100 g |

This coloring shampoo is applied for 30 minutes to a dark brown hair. After the exposure period, the hair is rinsed; the hair is then dyed with an intense auburn glint.

EXAMPLE A13

A coloring shampoo is prepared having the same composition as in Example A12, except that the mixture of compounds of Example 7 is used in place of the mixture of compounds of Example 4. The same coloration is obtained on the hair as for the composition of Example A12.

We claim:

1. A cosmetic composition for the hair selected from the group consisting of shampoo, after shampoo composition, conditioner, rinse, coloring shampoo and dyeing composition comprising from 0.1 to 30 weight percent based on the total weight of the composition of a surfactant or mixture of surfactants having the formula

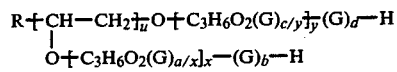

wherein

R represents a $C_{10}$-$C_{20}$ alkyl, alkenyl or alkylaryl radical,

G represents a $C_6H_{10}O_5$ radical derived from a hexose having the formula $C_6H_{12}O_6$, u represents 0 or 1, x represents 0 or an integer or decimal number less than or equal to 10, y represents an integer or decimal number equal to or less than 10, with the proviso that $1 \leq x+y \leq 10$, a, b, c and d each independently represent 0 or an integer or decimal number less than or equal to 5, with the proviso that $1 \leq a+b+c+d \leq 5$ and $$0.7 \leq \frac{x+y}{a+b+c+d} \leq 4$$

when u represents 0, each of x, a and b represents 0, and y represents an integer or decimal number ranging from 1.5 to 10;

when R represents alkylaryl, each of u, x, a and b represents 0;

the units $—C_3H_6O_2(G)_{a/x}$] mainly represent the following three structures:

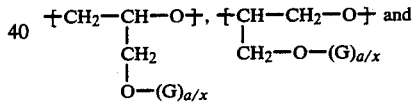

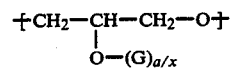

and the units $—C_3H_6O_2(G)_{c/y}$] mainly represent the following three structures:

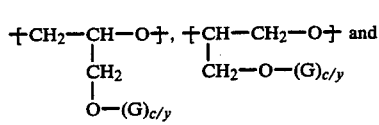

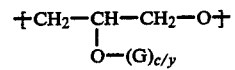

in a cosmetically acceptable vehicle selected from the group consisting of aqueous solution, hydroalcoholic solution, aqueous dispersion, hydroalcoholic dispersion, paste, gel, emulsion, solid and aerosol.

2. The cosmetic composition of claim 1 wherein said cosmetically acceptable vehicle is water or a hydroalcoholic solution.

3. The cosmetic composition of claim 1 wherein said surfactant or mixture of surfactants is present in an amount ranging from 0.5 to 20 weight percent based on the total weight of said composition.

4. The cosmetic composition of claim 1 which also includes a hair dyeing amount of a hair dye.

5. The cosmetic composition of claim 1 which also includes an anionic, cationic, nonionic or amphoteric polymer; a foam synergist; a protein; a thickener; or a superfatting agent; or a mixture thereof.

6. The cosmetic composition of claim 1 wherein said cosmetically acceptable vehicle is a mixture of water with a member selected from the group consisting of $C_1$–$C_6$ alcohol, $C_2$–$C_6$ diol and a glycol ether.

7. The cosmetic composition of claim 1 wherein R represents $C_{10}H_{21}$, $u=0$, $y=1.5$ and $c+d=1.5$.

8. The cosmetic composition of claim 1 wherein R represents $C_{12}H_{25}$, $u=0$, $y=2$ and $c+d=2$.

9. The cosmetic composition of claim 1 wherein R represents $C_{10}H_{21}$, $u=0$, $y=3.5$ and $c+d=2$.

10. The cosmetic composition of claim 1 wherein R is a hydrocarbon radical derived from oleic alcohol, $u=0$, $y=2$ and $c+d+1.5$.

11. The cosmetic composition of claim 1 wherein R represents $C_{10}H_{21}$, $u=1$, $(x+y)=3.5$ and $a+b+c+d=2$.

12. The cosmetic composition of claim 1 wherein R represents

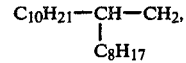

$u=0$, $y=6$ and $c+d=5$.

13. The cosmetic composition of claim 1 wherein R represents nonylphenyl, $u=0$, $y=2$ and $c+d=2$.

14. The cosmetic composition of claim 1 wherein R represents a hydrocarbon radical derived from oleic alcohol, $u=0$, $y=4$ and $c+d+2$.

15. A process for treating the hair comprising applying to said hair an effective amount of the cosmetic composition of claim 1.

* * * * *